US010315958B2

(12) United States Patent
Ritzberger et al.

(10) Patent No.: US 10,315,958 B2
(45) Date of Patent: Jun. 11, 2019

(54) $CEO_2$-STABILIZED $ZRO_2$ CERAMICS FOR DENTAL APPLICATIONS

(71) Applicant: Ivoclar Vivadent AG, Schaan (LI)

(72) Inventors: Christian Ritzberger, Grabs (CH);
Frank Rothbrust, Frastanz (AT);
Marcel Schweiger, Chur (CH); Nicolas Courtois, Villeurbanne (FR); Jérôme Chevalier, Rilieux-la Pape (FR); Helen Reveron, Lyons (FR); Wolfram Höland, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 1195 days.

(21) Appl. No.: 14/409,801

(22) PCT Filed: Jun. 20, 2013

(86) PCT No.: PCT/EP2013/062889
§ 371 (c)(1),
(2) Date: Dec. 19, 2014

(87) PCT Pub. No.: WO2013/190043
PCT Pub. Date: Dec. 27, 2013

(65) Prior Publication Data
US 2015/0191397 A1    Jul. 9, 2015

(30) Foreign Application Priority Data

Jun. 20, 2012    (EP) .................................. 12172818

(51) Int. Cl.
*C04B 35/48*    (2006.01)
*C04B 35/488*    (2006.01)
(Continued)

(52) U.S. Cl.
CPC ............ *C04B 35/488* (2013.01); *A61C 8/00* (2013.01); *A61C 8/0012* (2013.01);
(Continued)

(58) Field of Classification Search
CPC ..... C04B 35/48; C04B 35/482; C04B 35/484; C04B 35/486; C04B 35/488
(Continued)

(56) References Cited

U.S. PATENT DOCUMENTS 4,748,138 A * 5/1988 Watanabe ............. C04B 35/119
501/103
5,824,089 A * 10/1998 Rieger ................... A61L 27/10
424/423
(Continued)

FOREIGN PATENT DOCUMENTS

EP    2377506 A1    10/2011
EP    2500009 A1    9/2012
(Continued)

OTHER PUBLICATIONS

International Preliminary Report on Patentability of PCT/EP2013/062889, dated Dec. 23, 2014, 16 pages.
(Continued)

*Primary Examiner* — Noah S Wiese
(74) *Attorney, Agent, or Firm* — Ann M. Knab; Thad McMurray

(57) ABSTRACT

The present invention is directed to a porous pre-densified $CeO_2$ stabilized $ZrO_2$ ceramic having a density of 50.0 to 95.0%, relative to the theoretical density of zirconia, and an open porosity of 5 to 50% as well as to ceramic having a density of 97.0 to 100.0%, relative to the theoretical density of zirconia, and wherein the grains of the ceramic have an average grain size of 50 to 1000 nm, methods for the
(Continued)

Figure 1:
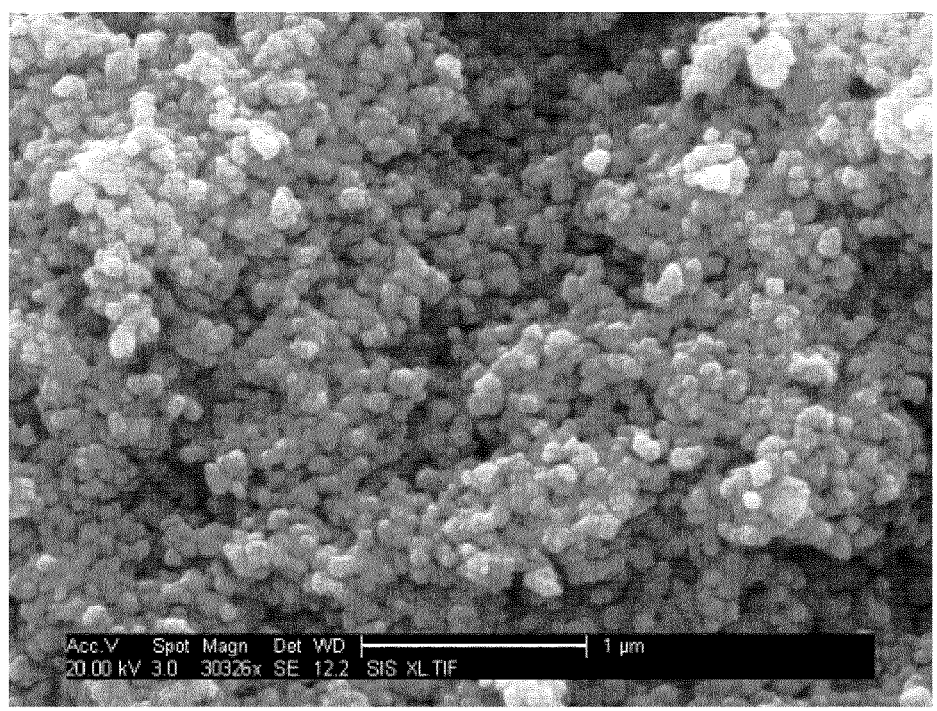

preparation of the pre-densified and densified ceramics and their use for the manufacture of dental restorations.

23 Claims, 3 Drawing Sheets

(51) Int. Cl.

| | |
|---|---|
| C04B 35/486 | (2006.01) |
| C04B 35/645 | (2006.01) |
| C04B 38/00 | (2006.01) |
| A61C 8/00 | (2006.01) |
| A61K 6/02 | (2006.01) |
| A61C 13/083 | (2006.01) |
| B82Y 30/00 | (2011.01) |
| C04B 111/00 | (2006.01) |

(52) U.S. Cl.
CPC ............ *A61C 13/083* (2013.01); *A61K 6/024* (2013.01); *A61K 6/025* (2013.01); *B82Y 30/00* (2013.01); *C04B 35/486* (2013.01); *C04B 35/645* (2013.01); *C04B 38/0038* (2013.01); *C04B 38/0054* (2013.01); *C04B 38/0058* (2013.01); *C04B 38/0061* (2013.01); *C04B 38/0067* (2013.01); *C04B 2111/00836* (2013.01); *C04B 2235/3201* (2013.01); *C04B 2235/3208* (2013.01); *C04B 2235/3217* (2013.01); *C04B 2235/3229* (2013.01); *C04B 2235/3232* (2013.01); *C04B 2235/3246* (2013.01); *C04B 2235/3272* (2013.01); *C04B 2235/3418* (2013.01); *C04B 2235/5445* (2013.01); *C04B 2235/604* (2013.01); *C04B 2235/612* (2013.01); *C04B 2235/6562* (2013.01); *C04B 2235/6565* (2013.01); *C04B 2235/6584* (2013.01); *C04B 2235/6581* (2013.01); *C04B 2235/6584* (2013.01); *C04B 2235/6587* (2013.01); *C04B 2235/661* (2013.01); *C04B 2235/663* (2013.01); *C04B 2235/666* (2013.01); *C04B 2235/72* (2013.01); *C04B 2235/765* (2013.01); *C04B 2235/77* (2013.01); *C04B 2235/781* (2013.01); *C04B 2235/785* (2013.01); *C04B 2235/786* (2013.01); *C04B 2235/96* (2013.01); *C04B 2235/963* (2013.01); *C04B 2235/9661* (2013.01)

(58) Field of Classification Search
USPC .................................................. 501/102, 103
See application file for complete search history.

(56) References Cited

U.S. PATENT DOCUMENTS

| | | | | |
|---|---|---|---|---|
| 6,087,285 | A * | 7/2000 | Oomichi | C04B 35/486 |
| | | | | 501/103 |
| 2005/0079971 | A1 | 4/2005 | Nawa | |
| 2008/0303181 | A1 | 12/2008 | Höland et al. | |
| 2009/0118114 | A1 * | 5/2009 | Zhang | A61L 27/10 |
| | | | | 501/135 |
| 2010/0126907 | A1 * | 5/2010 | Chun | C04B 35/482 |
| | | | | 208/123 |
| 2010/0292522 | A1 * | 11/2010 | Chun | C04B 35/488 |
| | | | | 585/648 |
| 2012/0094214 | A1 | 4/2012 | Zahid et al. | |

FOREIGN PATENT DOCUMENTS

| | | | |
|---|---|---|---|
| FR | 2946979 A1 | | 12/2010 |
| JP | 2007022889 A | * | 2/2007 |
| JP | 2007022889 A | | 2/2007 |
| WO | 0170643 A2 | | 9/2001 |
| WO | 2006024098 A1 | | 3/2006 |
| WO | 2010059322 A2 | | 5/2010 |

OTHER PUBLICATIONS

Xue, Miao, "Oral Biomaterials," World Publishing Corporation, Sep. 2006, p. 385, right column, lines 4-20.
Hu, Liang, "Chromium Resources and Advanced Chromium Alloy," Chemical Industry Press, Apr. 2010, p. 262, right column, lines 28-31.
R. Hannink et al., "Transformation Toughening in Zirconia-Containing Ceramics", Journal Am. Cer. Soc., 2000, vol. 83(3), pp. 461-487.
I. Denry et al., "State of the art of zirconia for dental applications", Dental Materials 24, 2008, pp. 299-307.
J. Chevalier et al., "Low-Temperature Degradation of Zirconia and Implications for Biomedical Implants", Annu. Rev. Mater. Res., 2007, 37, pp. 1-32.
K. Tsukuma et al., "Strength, fracture toughness and Vickers hardness of $CeO_2$-stabilized tetragonal $ZrO_2$ polycrystals (Ce-TZP)", Journal of Materials Science 20, 1985, pp. 1178-1184.
H. E. Attoui et al., "Static and cyclic crack propagation in Ce-TZP ceramics with different amounts of transformation toughening", Journal of the European Ceramic Society 27, 2007, pp. 483-486.
T. Xu et al., "Phase assembly and microstructure of $CeO_2$-doped $ZrO_2$ ceramics prepared by spark plasma sintering", Journal of the European Ceramic Society 25, 2005, pp. 3437-3442.
S.A. Cruz et al., "Nanostructured Spark Plasma Sintered Ce-TZP Ceramics", Journal of the American Ceramic Society, 2011, pp. 1-6.
S. Yin et al. "Preparation of porous ceria doped tetragonal zirconia ceramics by capsule fee hot isostatic pressing", British Ceramic Transactions, vol. 98(1), 1999, pp. 19-23.
Z. Zhou et al., "Preparation of machinable Ce-TZP/$CePO_4$, composite ceramics by liquid precursor infiltration", Journal of the European Ceramic Society, vol. 23(10), 2003, pp. 1649-1654.
S.G. Huang et al., "Composition design and mechanical properties of mixed (Ce, Y)-TZP ceramics obtained from coated starting powders", Journal of the European Ceramic Society, vol. 25(13), 2005, pp. 3109-3115.
Z. Xie et al., "Microwave processing and properties of ceramics with different dielectric loss", Journal of the European Ceramic Society, vol. 19(3), 1999, pp. 381-387.
E.N.S. Muccillo et al., "Synthesis of Zirconia-Based Solid Electrolyte Powders by the Coprecipitation Technique", Materials Science Forum, vol. 299-300, 1999, pp. 70-79.
M.M.R. Boutz et al., "The effect of ceria co-doping on chemical stability and fracture toughness of Y-TZP", Journal of Materials Science, vol. 30(7), 1995, pp. 1854-1862.
Jenq-Gong Duh et al., "Sintering, Microstructure, Hardness, and Fracture Toughness Behavior or $Y_2O_3$—$CeO_2$—$ZrO_2$", Journal of the American Ceramic Society, vol. 71(10), 1988, pp. 813-819.

* cited by examiner

CEO₂-STABILIZED ZRO₂ CERAMICS FOR DENTAL APPLICATIONS

CROSS-REFERENCE TO RELATED APPLICATIONS

This application is a National Stage application of International patent application PCT/EP2013/062889 filed on Jun. 20, 2013, which claims priority to European patent application No. 12172818.2 filed on Jun. 20, 2012, the disclosures of which are incorporated herein by reference in their entirety.

The present invention is directed to a porous, pre-densified as well as to a densified $CeO_2$-stabilized $ZrO_2$ ceramic, methods for their preparation and their use for the manufacture of dental restorations.

It is well known to use glass-ceramics and/or polycrystalline sintered ceramics, like $Al_2O_3$ or $ZrO_2$, as biomaterials for orthopedic or dental applications such as dental restorations. In particular, zirconia ($ZrO_2$) is unique amongst oxide ceramics due to its excellent mechanical properties, and a wide scientific background on $ZrO_2$ ceramics has been established since the 1980's.

Pure zirconia is of very limited interest as the tetragonal to monoclinic phase transformation occurring on cooling after sintering is accompanied by shear strain and volume expansion. This change of shape in the transforming volume can result in fracture and, hence, structural unreliability of fabricated components. Thus, it was a remarkable finding in the field of ceramics that the addition of oxides, such as $Y_2O_3$, $CeO_2$, MgO, CaO or other, in particular 4f-element oxides, to zirconia lowers the tetragonal to monoclinic transformation temperature and therefore stabilizes the tetragonal phase to a certain extent (see Hannink et al., J. Am. Ceram. Soc., 83[3] 461 (2000)). The tetragonal phase remains metastable and is able to transform under mechanical stress (stress-induced phase transformation). Thus, partially or fully stabilized zirconia exhibits a transformation toughening mechanism that acts to resist crack propagation. In particular, the stress-induced phase transformation is accompanied by a volumetric expansion which, at a crack tip, includes compressive stresses. Hence, the stress-induced phase transformation enhances the strength and fracture toughness and the transformation toughening mechanism combined with zirconia's bio-inertness led to the use of stabilized tetragonal zirconia polycrystals (TZP) in orthopedics and dental restorations.

Among tetragonal zirconia ceramics, the $Y_2O_3$-doped zirconia polycrystals (Y-TZP) takes today a preeminent position as an all-ceramic dental material. It usually contains 3 mol % yttria as a stabilizer (3Y-TZP) (see Denry et al., Dental Materials 24 (2008), 299-307). Furthermore, small amounts of alumina, such as 0.25 wt.-%, have been shown to act as sintering aid.

Moreover, Chevalier et al. (Annu. Rev. Mater. Res. 2007 (37), 1-32) found out that the presence of small alumina quantities (0.15 to 3 wt.-%) slows down the low temperature degradation (LTD) of zirconia which is assumed to be caused by oxygen vacancies formed by adding of $Y_2O_3$ as trivalent ion oxide into the $ZrO_2$ structure. Another promising way to reduce low temperature degradation is described to be the addition of other oxides such as $CeO_2$ to a Y-TZP to provide a Ce—Y-TZP.

Hannink et al. (see supra) describe that stabilization of tetragonal $ZrO_2$ in ceria-doped zirconia polycrystals (Ce-TZP) can occur over a wide range of compositions, like 12-20 mol % $CeO_2$, with 12 mol % Ce-TZP being preferred. The preparation of Ce-TZP is described to comprise firing for 1 h at about 1500° C. and the grain size after fabrication is reported to be in the range of 2 to 3 µm.

Monolithic $CeO_2$-stabilized tetragonal zirconia polycrystals are for example described by Tsukuma et al. (Journal of Materials Science 20 (1985) 1178-1184) and Attaoui et al. (Journal of the European Ceramic Society 27 (2007) 483-486). According to these documents, Ce-TZP is prepared by conventional pressing and sintering techniques, namely by an uniaxial compacting of the $CeO_2$-stabilized zirconia powders followed by an isostatic pressing to obtain green compacts which are then sintered in air at 1400 to 1600° C. for 2 h. The average grain-size of the obtained Ce-TZP samples is reported to be 0.5 to 2.5 µm, with generally being around 1.5 µm.

US 2008/0303181 teaches a dental material shaded to match the colors of natural dentition comprising Ce-TZP and a coloring agent. Likewise, the Ce-TZP is prepared by pressing and conventional sintering techniques such as compression of a shaped body, pre-sintering of the shaped body at a temperature of about 800 to 1300° C., soft machining of the pre-sintered body and then densely-sintering at a temperature of 1200 to 1600° C.

While the monolithic Ce-TZP ceramics prepared by pressing and conventional sintering techniques actually show a very high fracture toughness, a major disadvantage of this material is that its hardness and strength are relatively low.

Xu et al. (Journal of the European Ceramic Society 25 (2005) 3437-3442) deal with the microstructure of $CeO_2$-doped $ZrO_2$ ceramics prepared by spark plasma sintering (SPS) in comparison to the microstructure of ceramics prepared by hot-pressing. While the hot-pressed samples are reported to show no tetragonal $ZrO_2$ phase at all, the sample sintered by SPS was found to contain monoclinic and tetragonal $ZrO_2$ phases with a volume ratio of 2:1 and therefore resulted in an unsatisfactory low tetragonal phase content in view of the desired stress-induced phase transformation, in particular for dental applications. Another problem that limits the application of the above methods is the susceptibility of Ce-TZP to reduction. Since in the hot-pressing process as well as in the SPS process a graphite die is filled with the raw material powder, there is a strongly reducing atmosphere and reduction of $Ce^{4+}$ to $Ce^{3+}$ can easily be observed by the accompanying color change turning to brown which is an additional major drawback.

Cruz et al. (J. Am. Ceram. Soc. (2012), Volume 95, Issue 3, 901-906, DOI: 10.111/j.1551-2916.2011.04978.x) describe the preparation of 10 mol % $CeO_2$-doped $ZrO_2$ ceramics via SPS at 1200° C. with 5 min holding time or without holding time. While the relative density of the samples prepared without holding time is described to be only 97.9%, the sample sintered for 5 min is reported to be more dense, but characterized by the presence of significant amounts of a monoclinic phase and pyrochlore I phase, besides the desired tetragonal phase.

Thus, it is the object of the invention to avoid one or more disadvantages of the state of the art described above, and to provide a highly tetragonal $CeO_2$—$ZrO_2$ ceramic with an acceptable color and improved density and mechanical properties, especially improved hardness and strength, which make the material useful for dental applications.

This object is solved by a densified $CeO_2$-stabilized $ZrO_2$ ceramic according to claims 11 to 16 and a method for its preparation according to claim 17 or 18. The invention is further directed to a porous, pre-densified $CeO_2$-stabilized $ZrO_2$ ceramic according to claims 1 to 7 and a method for its preparation according to claims 8 to 10. The invention also relates to the use of the porous $CeO_2$—$ZrO_2$ ceramic as well as the densified $CeO_2$—$ZrO_2$ ceramic according to claim 19.

In a first aspect, the invention is directed to a pre-densified $CeO_2$—$ZrO_2$ ceramic, namely a porous $CeO_2$-stabilized $ZrO_2$ ceramic having a density of 50.0 to 95.0%, preferably 60.0 to 90.0%, more preferably 70.0 to 85.0%, relative to the theoretical density of zirconia, and an open porosity of 5 to 50%, preferably 10 to 30%, more preferably 14 to 25%, and most preferably 15 to 23%.

The porous ceramic according to the invention preferably has a closed porosity of less than 5%, more preferably less than 2% and most preferably less than 1%.

It is also preferred that the open pores of the porous ceramic according to the invention are characterized by a mean pore diameter of 10 to 500 nm, more preferably 25 to 300 nm and most preferably 50 to 200 nm.

Moreover, the porous ceramic according to the invention is preferably in the form of equiaxed, fine-grained polycrystalline aggregates. In particular, the grains of the porous ceramic have an average grain size of 10 to 500 nm, preferably 20 to 400 nm or 25 to 300 nm, more preferably 50 to 200 nm, like 60 to 200 nm or 80 to 180 nm.

Furthermore, it is preferred that tetragonal $ZrO_2$ is the main crystalline phase of the porous ceramic. Preferably, the porous ceramic comprises tetragonal $ZrO_2$ in an amount of 50 to 100 vol.-%, preferably 70 to 100 vol.-%, more preferably 90 to 100 vol.-% and most preferably 95 to 100 vol.-%, like 97 to 100 vol.-%, based on the total volume of crystals of the ceramic.

It has been surprisingly found that the specific combination of density and open porosity of the pre-densified, porous ceramic according to the invention results in that the porous ceramic is very suitable for the preparation of a dense $CeO_2$-stabilized $ZrO_2$ ceramic having improved properties, such as improved microstructure and mechanical properties, and in particular meeting the need for translucency of dental restorations.

Preferably, the porous $CeO_2$-stabilized $ZrO_2$ ceramic is in the form of a pre-densified blank or body. The porous pre-densified Ce-TZP can be shaped to a dental restoration by e.g. milling or grinding, preferably by machining using CAD/CAM technology, particularly if the Vickers hardness $HV_5$ is lower than 800 $daN/mm^2$, preferably lower than 500 $daN/mm^2$.

The invention is also directed to a method for preparing the porous $CeO_2$-stabilized $ZrO_2$ ceramic according to the invention comprising (a) pre-densifying a $CeO_2$-containing $ZrO_2$ starting material to provide the porous ceramic.

Typically, a powder raw material or compact green comprising $ZrO_2$ and $CeO_2$ is used as $CeO_2$-containing $ZrO_2$ starting material. Preferably, the starting material comprises about 6 to 18 mol % of $CeO_2$, more preferably 10 to 14 mol % of $CeO_2$, such as about 12 mol % of $CeO_2$. The starting material is pre-densified, i.e. its density is increased by pressure, heat, radiation or combinations thereof. In accordance with the invention, step (a) is performed in such a way that at the end of pre-densifying the ceramic is not in the form of a fully or nearly fully dense $CeO_2$—$ZrO_2$ ceramic. In fact, at the end of step (a) the ceramic is characterized by the above described density of 50 to 95%, preferably 60 to 90%, more preferably 70 to 85%, relative to the theoretical density of zirconia.

In a preferred embodiment, the pre-densifying step (a) is performed by spark plasma sintering (SPS).

Generally, spark plasma sintering is a rather fast sintering technique, wherein pulsed DC current passes through a graphite die containing the starting material so that heat is generated internally and high heating and cooling rates can be obtained. According to a preferred embodiment of SPS method of step (a), the $CeO_2$-containing $ZrO_2$ starting material is heated to a sintering temperature of about 950 to 1350° C., preferably about 1050 to 1250° C. Moreover, it is preferred that the starting material is heated at a heating rate of 1 to 400° C./min, preferably 5 to 100° C./min, more preferably 20 to 100° C./min or 50 to 100° C./min. Furthermore, it is preferred that pre-densification of step (a) is carried out without any holding time, i.e. that the temperature is decreased as soon as the maximum pre-densification temperature is arrived.

In addition to heating, the SPS method of step (a) preferably comprises pressing the $CeO_2$-containing $ZrO_2$ starting material at a pressure of 0 to 500 MPa, like 20 to 300 MPa, particularly 50 to 250 MPa.

The pulsed DC current of the SPS method can be characterized by a voltage from 1 to 20 V and/or by an amperage from 0.1 to 10 kA. Moreover, the sequence of pulses applied to the starting material may be any suitable sequence such as 1 to 30 ms with current (on) and 1 to 30 ms with no current (off), for instance 5 to 15 ms with current (on) and 1 to 10 ms with no current (off), such as 10 ms with current (on) and 5 ms with no current (off).

Since suitable pre-densifying methods according to the invention, such as spark plasma sintering, are usually carried out in non-oxidizing atmospheres or even reducing environments, reduction of $Ce^{4+}$ to $Ce^{3+}$ may take place during step (a). Such a reduction can be easily observed in the pre-densified ceramic by the accompanying color change of the sample. Besides color, reduction of $Ce^{4+}$ to $Ce^{3+}$ may also affect low temperature degradation properties and the stability of the tetragonal phase of $ZrO_2$ at room temperature. Thus, in one embodiment the method for preparing the porous ceramic comprises (b) re-oxidizing the porous ceramic obtained in step (a).

Such a re-oxidation can be conducted by heating the pre-densified ceramic obtained in step (a) in an oxidizing atmosphere, in particular air. Preferably, the ceramic obtained in step (a) is heated to a temperature of 400 to 1200° C., more preferably 600 to 1000° C., like about 800° C. In particular, the re-oxidation should be conducted so that no further densification takes place during step (b). If step (a) is performed by spark plasma sintering at a relatively low temperature, such as 1100° C. or 1150° C., the obtained pre-densified porous ceramic is usually of rather light color, e.g. light grey, and there is then generally no need for a re-oxidation step (b).

In a further aspect, the invention is directed to a densified $CeO_2$-stabilized $ZrO_2$ ceramic which can be prepared from the porous ceramic according to the first aspect. The densified $CeO_2$-stabilized $ZrO_2$ ceramic has a density of 97.0 to 100.0%, like 98.0 to 100.0%, preferably 99.0 to 100.0%, like 99.5 to 100.0%, more preferably about 100.0%, relative to the theoretical density of zirconia. The densified $CeO_2$-stabilized $ZrO_2$ ceramic is also characterized in that it comprises grains having an average grain size of 50 to 1000 nm like 600 to 1000 nm, preferably 100 to 800 nm, more preferably 400 to 700 nm.

Preferably, tetragonal $ZrO_2$ is substantially the only crystalline $ZrO_2$ phase of the densified ceramic. Accordingly, the densified ceramic preferably comprises tetragonal $ZrO_2$ in an amount of 90 to 100 vol.-%, preferably 95 to 100 vol.-%, more preferably 97 to 100 vol.-%, like 98.0 to 100 vol.% or 99.0 to 100.0 vol.-%, such as about 100 vol.-%, based on the total volume of crystals of the densified ceramic.

In one embodiment, the microstructure of the densified ceramic can further be characterized in that the residual pores have a mean diameter of less than 150 nm, like 5 to less than 150 nm or 10 to less than 150 nm, preferably less than 100 nm, more preferably less than 80 nm, and most preferably less than 20 nm, such as about 10 nm. Furthermore, it is also preferred that the open porosity and the closed porosity of the densified ceramic according to the invention are each lower than 1%.

Without wishing to be bound to any particular theory, it is assumed that due to the combination of very low porosity content and very small grain size the densified ceramic according to the invention has improved mechanical and optical properties, such as translucency.

In particular, the densified ceramic according to the invention has a Vickers hardness of more than 8,000 MPa, like 8,500 to 12,000 MPa, preferably 8,500 to 11,000 MPa and more preferably 8,800 to 9,500 MPa.

It is also preferred that the densified ceramic according to the invention has a biaxial flexural strength of more than 700 MPa, such as 700 MPa to about 900 MPa like 700 MPa to about 800 MPa.

Moreover, the densified ceramic is characterized in that it has a light color suitable for dental applications, although it can be prepared by reducing sintering techniques, which are usually reported to result in an undesired color change. Preferably, the densified ceramic of the invention has a color characterized by L* values of 80 to 95, a* values of −4 to 0 and b* values of 14 to 25.

Preferably, the porous ceramic according to the invention as well as the densified ceramic according to the invention comprise 6 to 18 mol %, more preferably 8 to 16 mol %, like 9.0 to 15.0 mol % or 10 to 14 mol %, like 11.0 to 14.0 mol %, such as about 12 mol % of $CeO_2$, based on the total ceramic composition. Furthermore, it is preferred that the porous ceramic according to the invention as well as the densified ceramic according to the invention comprise 82 to 94 mol %, more preferably 86 to 90 mol %, such as about 88 mol.% of $ZrO_2$ or a mixture of $ZrO_2$ with small amounts of $HfO_2$, based on the total ceramic composition. In addition to $CeO_2$ the ceramics can comprise 0 to 0.50 wt.-%, preferably 0.10 to 0.40 wt.-%, such as 0.30 to 0.40 wt.-% of $Al_2O_3$, and/or 0 to 0.50 wt.-%, preferably 0.10 to 0.20 wt.-% of $SiO_2$. Moreover, the ceramics can comprise small amounts of further components, additives or imputities like metal oxides independently selected from the group consisting of $Fe_2O_3$, $TiO_2$, $Na_2O$, CaO, $La_2O_3$ and mixtures thereof.

The densified $CeO_2$-stabilized $ZrO_2$ ceramic according to the invention can be prepared by a method comprising
(a') providing a porous $CeO_2$-stabilized $ZrO_2$ ceramic according to the first aspect of the invention or obtainable by a method described above for preparing the porous $CeO_2$-stabilized $ZrO_2$ ceramic,
(c) optionally shaping the porous ceramic provided in step (a'), and
(d) densifying the porous ceramic provided in step (a') or obtained in step (c) to obtain the densified $CeO_2$-stabilized $ZrO_2$ ceramic.

In step (a') a porous $CeO_2$-stabilized $ZrO_2$ ceramic according to the first aspect of the invention is provided, preferably by preparing it using the above described steps of pre-densifying (a) and optional re-oxidizing (b).

In optional step (c), the porous $CeO_2$—$ZrO_2$ ceramic can be shaped, preferably by machining like direct ceramic machining. Briefly, a die or a wax pattern of the desired dental restoration is scanned, an enlarged restoration is designed by computer software (CAD) and the pre-densified, porous ceramic provided in step (a') is milled by computer aided machining (CAM).

In step (d), the pre-densified, porous ceramic is further densified to arrive at the final density. According to a preferred embodiment, densifying in step (d) is performed in an oxygen-containing atmosphere, preferably by sintering in an atmosphere having an oxygen partial pressure of more than 5 kPa, such as more than 10 or more than 15 kPa, more preferably by sintering in air. It is particularly preferred to sinter the porous ceramic provided in step (a') or obtained in step (c) by heating it to a temperature from about 1100 to about 1550° C., preferably 1200 to 1500° C. Preferably, the heating rate applied in step (d) is 1 to 100 K/min, 2 to 50 K/min or 5 to 20 K/min. Moreover, it is preferred to hold the maximum sinter temperature for about 0 to 5 h, preferably 0 to 3 h. It is particularly preferred that step (d) is performed in the absence of any periodic current pulses applied to the porous ceramic.

Thus, the invention is particularly directed to a method for preparing a densified $CeO_2$-stabilized $ZrO_2$ ceramic comprising
(a) pre-densifying a $CeO_2$-containing $ZrO_2$ starting material to provide a pre-densified, porous $CeO_2$-stabilized $ZrO_2$ ceramic body having a density of 50 to 95%, preferably 60 to 85%, relative to the theoretical density of zirconia, and an open porosity of 5 to 50%, preferably 10 to 30%, more preferably 14 to 25%, most preferably 15 to 23%.;
(b) optionally re-oxidizing the pre-densified, porous ceramic body obtained in step (a);
(c) optionally shaping the pre-densified, porous ceramic body obtained in step (a) or (b), preferably by machining; and
(d) densifying the pre-densified, porous ceramic body obtained in step (a), (b) or (c) to obtain the densified $CeO_2$-stabilized $ZrO_2$ ceramic, preferably by sintering in an oxygen-containing atmosphere.

It has surprisingly found that, the combination of the porosity controlling pre-densifying step (a) and the densifying step (d) provides a highly dense $CeO_2$—$ZrO_2$ ceramic with submicrometric grain size and improved mechanical properties. In particular, the densified ceramic according to the invention is characterized by a hardness of more than 9 GPa and an acceptable color avoiding orange to dark brown colors.

Hence, the invention is also directed to the use of a porous $CeO_2$-stabilized $ZrO_2$ ceramic according to the first aspect of the invention or of a densified $CeO_2$-stabilized $ZrO_2$ ceramic according to the second aspect of the invention for the preparation of dental restorations, preferably dental frameworks, dental abutments and dental implants, as well as for the manufacture of precision devices, such as watches, or medical devices.

The above described properties of the pre-densified, porous ceramic according to the invention and of the densified ceramic according to the invention are determined as follows.

As used herein, the term "density" refers to the bulk density of a ceramic according to ASTM C373. Thus, the density is determined by using the ASTM procedure C373, which is based on Archimedes' principle. Unless otherwise indicated, densities specified herein are relative to the theoretical density of zirconia which is 6.23 g/cm$^3$.

The open porosity and the closed porosity of the ceramics are each determined by using the ASTM procedure C373.

For microstructure analysis, X-ray diffractograms are recorded (Bruker D8 Advance with Cu Kα radiation). The amount of tetragonal $ZrO_2$ is determined by Retvield analysis as described in Cruz et al. (see supra).

The observed crystal phases summarized in Tables 2 and 3 are identified by different letters: T for tetragonal phase, M for monoclinic phase and C for a cubic Ce-enriched phase which appears close to the Zr—Ce—O cubic solid solution as described by Xu et al. (see supra).

The average grain size and the mean pore diameter of the ceramics are determined by SEM imaging (Zeiss Supra 40VP).

The average grain size is determined by an image analysis using SEM and an image treatment software (ImageJ). In particular, the average grain size is the arithmetical mean of the diameter of 30 grains that are statistically selected from SEM images of three different fracture surfaces of the sample taking into account a Lince program correction factor of 1.2 on the diameters obtained from 2D SEM picture analysis.

The mean pore diameter is determined by an image analysis using SEM and an image treatment software (ImageJ). In particular, the mean pore diameter is the arithmetical mean of the diameter of 30 pores that are statistically selected from SEM images of three different fracture surfaces of the sample taking into account a Lince program correction factor of 1.2 on the diameters obtained from 2D SEM picture analysis.

The Vickers hardness of a sample is determined using a Test-well FV-700 indenter with a load of 30 kg and a dwell time of 10 s. At least 5 indents per sample are effected.

The biaxial flexural strength of a ceramic is determined in accordance with ISO6872-2008 by a piston-on-three-ball test. Loading is performed at 1 mm/min up to failure.

The determination of color values is done with a CM-3700d spectrometer (Company Konica-Minolta). The values L*, a*, b* are measured according to the DIN5033 and DIN6174 standard.

The special settings for color measurements are as follows:

Lighted up area/measuring aperture: 7 mm×5 mm

Type of measure: remission/reflection

Measuring number: single measurement

Measuring range: 400-700 nm

Color of the background: L*=93.11 a*=−0.64 b*=4.22

The sample size for color measurements is as follows:

Diameter: Ø15-20 mm

Thickness: 2 mm±0.025 mm

Plane parallel: ±0.05 mm

Surface roughness: ~18 μm

The invention is further illustrated by the following examples.

EXAMPLES

Example 1 i) Raw Material

A non-spray dried submicrometric powder comprising about 88 mol % of zirconium oxide and about 12 mol % of cerium oxide produced by Daiichi, Japan was used as starting raw material (Daiichi CEZ-12-1). The exact composition of the raw material is given in Table 1.

TABLE 1

| Composition of Daiichi CEZ-12-1 raw material in wt.-% | | | | | | | | |
|---|---|---|---|---|---|---|---|---|
| $ZrO_2$ + $HfO_2$ | $CeO_2$ | $Al_2O_3$ | $SiO_2$ | $Fe_2O_3$ | $TiO_2$ | $Na_2O$ | CaO | $H_2O$ |
| 83.4 ± 0.4 | 15.6-16.4 | 0.30 | 0.15 | 0.01 | 0.15 | 0.03 | 0.05 | 0.50 | ii) Pre-densifying

In the first step, the 12Ce-TZP powder was pre-densified by using spark plasma sintering (SPS) techniques. A graphite cylindrical die with an internal diameter of 20 mm was used. A graphite foil was rolled and slid into the die to cover its internal surface. Then, a plunger covered by a circular piece of graphite foil was introduced into the die. Next, 6 g of the 12Ce-TZP powder were introduced into the die by means of a spatula and finally a second plunger covered by a graphite foil was placed above the powder. This assembly was put in the SPS apparatus (HP D25 from FCT GmbH, Germany) between the pushing electrodes. The vacuum chamber was closed and the parameters were set. The chosen atmosphere was a vacuum of $10^{-2}$ bar, and the pulsed direct current was set to the following sequence: 10 ms time on, then 5 ms time off. The sintering was performed with a heating rate of 50° C./min. A pressure of 76 MPa was applied before heating and maintained during sintering. The attained sintering temperature was 1150° C., measured by pyrometer. Once this temperature attained, the temperature was reduced down to room temperature in 13 minutes. After sintering, the sample was removed from the die and cleaved graphite foil chips were removed.

iii) Densifying

In a second step, the spark plasma sintered sample was put in a crucible on a bed of ceramic powder (12 $CeO_2$—$ZrO_2$) having the same chemical composition as the sample. Then, the crucible with the sample was placed in a furnace with air circulation, heated at 5° C./min up to 1300° C. and held for 2 hours at this temperature. Finally, the heating was stopped and the furnace was cooled down to room temperature.

Comparative Example 1

As a modification of the powder from Example 1, commercial powder Daiichi CEZ-12-2 was used in this comparative example instead of Daiichi CEZ-12-1. The composition of Daiichi CEZ-12-2 was similar to that of Daiichi CEZ-12-1, but the powder additionally contained 4,5 wt.-% of organic molecules that enhances its pressing behavior. This powder was uniaxially die-pressed into a disk with a pressure of 50 MPa. Then, a cold isostatic pressing was performed with a pressure of 280 MPa. The sintering was performed according to the following process: heating up to 600° C. at 1° C./min, dwelling for 2 hours, heating up to 1430° C. at 5° C./min, dwelling for 2 hours and finally cool down to room temperature at 8° C./min.

Example 2

A pressed pellet of the Daiichi CEZ-12-2 powder was prepared by uniaxial die-pressing with a pressure of 200 MPa. Debindering was performed according to the following procedure: heating up to 600° C. at 1° C./min, dwelling for 2 hours and then cooling at 5° C./min. The debindered pellet was then processed into a densified $CeO_2$-stabilized $ZrO_2$ ceramic sample using the steps of pre-densifying by SPS and subsequent densifying as described in Example 1.

Example 3

A densified $CeO_2$-stabilized $ZrO_2$ ceramic sample was prepared as described in Example 2, with the exception that in the SPS process step a peak temperature of 1150° C. and a heating rate of 20° C./min were used.

Example 4

A series of 10 densified $CeO_2$-stabilized $ZrO_2$ ceramic samples having a thickness of 1.2 mm and a diameter of 13 mm was prepared as described in Example 2. After sintering, biaxial testing specimen were prepared as described in ISO6872-2008.

Comparative Example 2

A densified $CeO_2$-stabilized $ZrO_2$ ceramic sample was prepared as described in Example 1, with the exception that in the SPS process a peak temperature of 1250° C. and a heating rate of 20° C./min were used.

Comparative Example 3

A series of 10 pellets of Daiichi CEZ-12-2 were prepared by CAD-CAM machining (Cerec 3 milling unit, Sirona, Austria) of presintered blocks. The presintered blocks were obtained by shaping via uniaxial pressing at 250 MPa and presintering at 1000° C. for 2 hours. After presintering and CAD-CAM machining the disks were sintered at 1400° C. for 2 hours, and finally prepared as described in ISO6872-2008 for biaxial flexural testing.

Properties

Some properties of ceramic samples in the pre-densified state are summarized in Table 2.

TABLE 2

Properties of the samples after pre-densifying

|  | Density | Open porosity | Closed porosity | Crystal phases |
|---|---|---|---|---|
| Example 1 | 79.4% | 20.2% | 0.4% | T |
| Example 2 | 84% | 21.8% | 0.2% | T |
| Example 3 | 81.6% | 17.75% | 0.65% | T + M |
| Example 4 | 80.0% | 19.5% | 0.5% | T |
| Comparative example 2 | 96.7% | 0.7% | 2.6% | T + M + C |

As can be seen from Table 2, after SPS treatment the samples of Examples 1 to 4 have a density of about 75 to 85% of the theoretical density and a closed porosity of less than 1%.

Table 3 summarizes properties of samples in the fully densified state.

TABLE 3

Properties of the samples after densifying

|  | Density | Open porosity | Closed porosity | Crystal phases |
|---|---|---|---|---|
| Example 1 | 100% | 0% | 0% | T |
| Example 2 | 100% | 0% | 0% | T |
| Example 3 | 100% | 0% | 0% | T |
| Example 4 | >99.5% | 0% | 0% | T |
| Comparative example 1 | 98.5% | 0.3% | 1.2% | T |
| Comparative example 2 | 95.6% | 0.4% | 4% | T |
| Comparative example 3* | >99.5% | 0% | 4.0% | T |

*Average grain size of densified ceramic was 1.1 μm.

After the second heat treatment, the samples of Examples 1 to 5 were fully dense (100% of theoretical density). Moreover, after the second heat treatment only tetragonal phases have been observed in all samples.

FIG. 1 shows an SEM image of the pre-densified $CeO_2$—$ZrO_2$ ceramic obtained in Example 1. It can be seen that the microstructure of this sample is characterized by very fine, spherical Ce-TZP nanoparticles having a diameter of about 100 nm.

Figure 2:
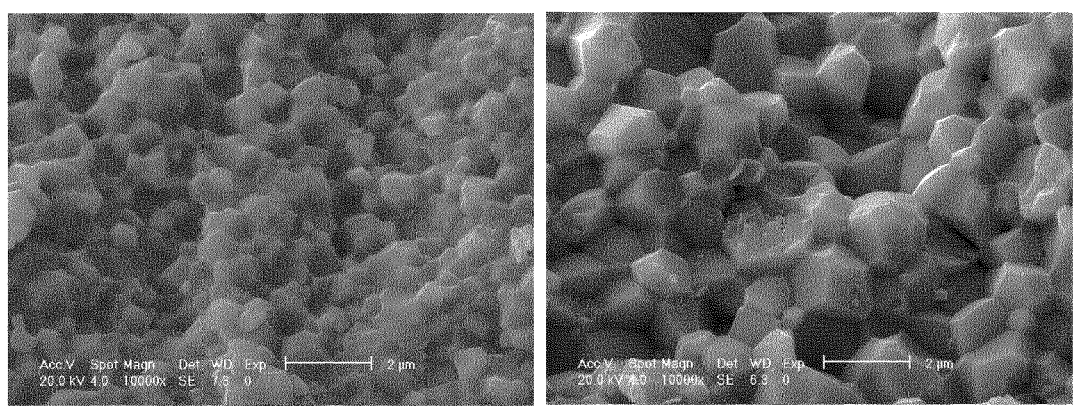

FIG. 2 shows an SEM image of the densified $CeO_2$—$ZrO_2$ ceramic obtained in Example 1 (left picture) and an SEM image of the $CeO_2$—$ZrO_2$ ceramic obtained in Comparative Example 1 (right picture). As can be seen, the densification was nearly complete (close to 100% of theoretical density) and only some very small pores of less than 80 nanometers in their biggest dimension were visible in the sample prepared according to the invention (Example 1). Moreover, the grain sizes obtained in the sample of Example 1 are about half of the grain sizes obtained for the sample of Comparative Example 1. The average grain size of the densified ceramic according to Example 1 was 0.6±0.1 μm.

Figure 3:
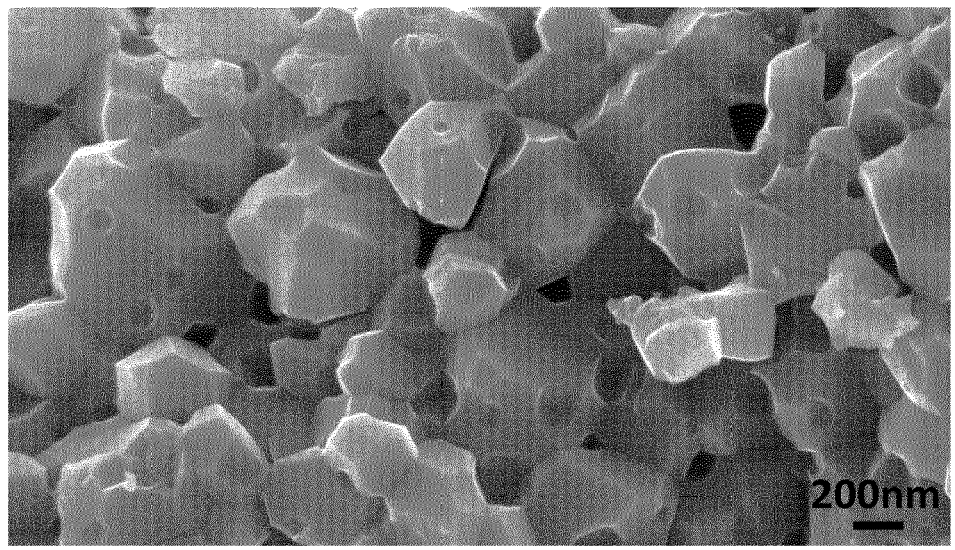

FIG. 3 shows an SEM image of the densified $CeO_2$—$ZrO_2$ ceramic obtained in Comparative Example 2. In contrast to the fully densified sample of Example 1, the ceramic of Comparative Example 2 is characterized by several, clearly visible pores of about 200 nm.

The mechanical properties of the samples obtained in the examples are given in Table 4.

TABLE 4

Mechanical properties of the samples after densifying

|  | Vickers Hardness (GPa) | Standard deviation | Biaxial flexural strength (MPa) | Standard deviation |
|---|---|---|---|---|
| Example 1 | 9.070 | 47 |  |  |
| Example 2 | 9.013 | 38 |  |  |
| Example 3 | 9.096 | 43 |  |  |
| Comparative Example 1 | 8.390 | 23 | 624 | 35 |
| Example 4 |  |  | >720 | 35 |

The invention claimed is:

1. Porous $CeO_2$-stabilized $ZrO_2$ ceramic having a density of 50.0 to 95.0%, relative to the theoretical density of zirconia, and an open porosity of 5 to 50%, wherein the pores of the ceramic have a mean pore diameter of 10 to 500 nm.

2. Porous ceramic according to claim 1 having a density of 60.0 to 90.0%.

3. Porous ceramic according to claim 1 having an open porosity of 10 to 30%.

4. Porous ceramic according to claim 1 having a closed porosity of less than 5%.

5. Porous $CeO_2$-stabilized $ZrO_2$ ceramic having a density of 50.0 to 95.0%, relative to the theoretical density of zirconia, and an open porosity of 5 to 50%, wherein grains of the ceramic have an average grain size of 10 to 500 nm.

6. Porous ceramic according to claim 1 comprising tetragonal $ZrO_2$ in an amount of 50 to 100 vol.-%, based on the total volume of crystals of the ceramic.

7. Porous ceramic according to claim 2 having a density of 70.0 to 85.0%.

8. Porous ceramic according to claim 3 having an open porosity of 14 to 25%.

9. Porous ceramic according to claim 3 having an open porosity of 15 to 23%.

10. Porous ceramic according to claim 4 having a closed porosity of less than 2%.

11. Porous ceramic according to claim 4 having a closed porosity of less than 1%.

12. Porous ceramic according to claim 1, wherein the pores of the ceramic have a mean pore diameter of 25 to 300 nm.

13. Porous ceramic according to claim 1, wherein the pores of the ceramic have a mean pore diameter of 50 to 200 nm.

14. Porous ceramic according to claim 5, wherein the grains of the ceramic have an average grain size of 25 to 300 nm.

15. Porous ceramic according to claim 5, wherein the grains of the ceramic have an average grain size of 50 to 200 nm.

16. Porous ceramic according to claim 6 comprising tetragonal $ZrO_2$ in an amount of 70 to 100 vol.-%, based on the total volume of crystals of the ceramic.

17. Porous ceramic according to claim 6 comprising tetragonal $ZrO_2$ in an amount of 90 to 100 vol.-%, based on the total volume of crystals of the ceramic.

18. Method for preparing a porous $CeO_2$-stabilized $ZrO_2$ ceramic having a density of 50.0 to 95.0%, relative to the theoretical density of zirconia, and an open porosity of 5 to 50%, wherein the pores of the ceramic have a mean pore diameter of 10 to 500 nm comprising (a) pre-densifying a $CeO_2$-containing $ZrO_2$ starting material to provide the porous ceramic.

19. Method according to claim 18, wherein pre-densifying in step (a) is performed by spark plasma sintering which includes heating the $CeO_2$-containing $ZrO_2$ starting material to a sintering temperature of about 950 to 1350° C. and/or heating the $CeO_2$-containing $ZrO_2$ starting material at a heating rate of 1 to 400° C./min.

20. Method according to claim 18, comprising (b) re-oxidizing the porous ceramic obtained in step (a).

21. Method according to claim 19, wherein pre-densifying in step (a) is performed by spark plasma sintering the $CeO_2$-containing $ZrO_2$ starting material to a sintering temperature of about 1050 to 1250° C., and/or heating the $CeO_2$-containing $ZrO_2$ starting material at a heating rate of 5 to 100° C./min.

22. Method according to claim 19, wherein pre-densifying in step (a) is performed heating the $CeO_2$-containing $ZrO_2$ starting material at a heating rate of 50 to 100° C./min.

23. Method of using a porous $CeO_2$-stabilized $ZrO_2$ ceramic having a density of 50.0 to 95.0%, relative to the theoretical density of zirconia, and an open porosity of 5 to 50%, wherein grains of the ceramic have an average grain size of 10 to 500 nm, for the preparation of dental restorations, dental frameworks, dental abutments and dental implants.

* * * * *